United States Patent [19]

Herold et al.

[11] Patent Number: 5,505,196
[45] Date of Patent: Apr. 9, 1996

[54] DEVICE FOR INHALATION

[75] Inventors: Heiko Herold, Neuss; Axel Wollenschläger, Bergisch Gladbach; Ahmed Hegazy; Matthias Herboth, both of Leverkusen; Reiner Diederich, Wesseling; Roland Kleissendorf, Bergisch Gladbach; Alfred von Schuckmann, Kevelaer, all of Germany

[73] Assignee: Bayer Aktiengesellschaft, Leverkusen, Germany

[21] Appl. No.: 344,049

[22] Filed: Nov. 23, 1994

[30] Foreign Application Priority Data

Nov. 30, 1993 [DE] Germany ............ 43 40 768.4

[51] Int. Cl.⁶ ................................................. A61M 15/00
[52] U.S. Cl. ....................... 128/203.15; 128/203.12; 128/203.23; 128/203.21
[58] Field of Search ............... 128/203.12, 203.14, 128/203.15, 203.18, 203.19, 203.21, 203.22, 203.23, 203.24, 203.28, 204.13

[56] References Cited

U.S. PATENT DOCUMENTS

| | | | |
|---|---|---|---|
| 3,837,341 | 9/1974 | Bell | 128/203.21 |
| 4,907,583 | 3/1990 | Wetterlin et al. | 128/203.12 |
| 5,113,855 | 5/1992 | Newhouse | 128/203.12 |
| 5,243,970 | 9/1993 | Ambrosio et al. | 128/203.12 |
| 5,301,666 | 4/1994 | Lerk et al. | 128/203.21 |
| 5,320,714 | 6/1994 | Brendel | 128/203.15 |
| 5,341,800 | 8/1994 | Clark et al. | 128/203.15 |

FOREIGN PATENT DOCUMENTS

| | | |
|---|---|---|
| 0505321 | 9/1992 | European Pat. Off. . |
| 4004904 | 9/1990 | Germany . |
| 2165159 | 4/1986 | United Kingdom . |
| 8201470 | 5/1982 | WIPO . |
| 9200771 | 1/1992 | WIPO . |
| 09322 | 6/1992 | WIPO ................. 128/203.15 |

*Primary Examiner*—Edgar S. Burr
*Assistant Examiner*—William J. Deane, Jr.
*Attorney, Agent, or Firm*—William C. Gerstenzang; Sprung Horn Kramer & Woods

[57] ABSTRACT

The device for inhalation of a powdery, pharmacologically active drug consists of a supply container (3) for the drug (4), a manually actuated metering unit for providing a portioned-off quantity of inhalation substance which is picked up by the air current drawn in during inhalation and is swirled, an air inlet channel (9), a swirl chamber (W), and a connection channel (8) between the swirl cheer (W) and the metering unit, as well as a mouthpiece channel issuing from the swirl chamber (W). The metering unit here consists of a metering drum (D) which has, in its interior (5), a supply container (3) for the drug. Furthermore, the air inlet channel (9) and the connection channel (8) are arranged in such a way that they run towards each other in a V-shape. During a metering procedure, a portioned-off quantity of drug for inhalation present in the shape of a dome is provided in each case at the apex of the two air channels (8) and (9) running towards each other in a V-shape.

15 Claims, 8 Drawing Sheets

DEVICE FOR INHALATION

The invention relates to a device for inhalation of a powdery, pharmacologically active drug, consisting of a supply container for the drug, a manually actuated metering unit for providing a portioned-off quantity of inhalation substance which is picked up by the air current drawn in during inhalation and is swirled, an air inlet channel, a swirl chamber, and a connection channel between the swirl chamber and the metering unit, as well as a mouthpiece channel issuing from the swirl chamber.

A device of this type is known from DE-OS (German Published Specification) 4 004 904. The drug supply is kept ready there at the periphery of the metering drum and is readjusted radially. The interior of the metering drum contains a control device for active discharge of the portioned-off inhalation quantity of drug from radially outwardly directed, open metering recesses. For this purpose, slides forming the base of the metering recesses, which are arranged distributed at uniform angles, are centrally cam-controlled. The outlay in this regard is considerable, especially since the control mechanism is released by an actuation key taking up almost the whole of one longitudinal side of the device. Air inlet channel and connection channel run at an obtuse angle and tangent to the metering drum, this air course continuing via a swirl chamber, formed as a secondary cavity, essentially straight as far as the other end of the device. The drug transfer point lies near the open intake end and the substance can easily fall out there unused. In addition, the metered inhalation quantities of drug can add up as a result of the forced emptying of the metering recess; this can therefore lead to a dangerous overdose. In terms of volume, only a fraction of the device designed in pocket format remains for holding a supply. The method of handling is not clear.

The object of the invention is to design a device of the generic type which, being of simplified construction, is more advantageous and safer to use, in particular also to improve the device in terms of flow technology, and to keep the effect constant by means of complete discharge of the portioned-off inhalation quantity of drug.

This object is achieved by the invention specified in claim 1.

The claims subsequent thereto present further advantageous embodiments of the device according to the invention.

As a result of such an embodiment, a device of the generic type is obtained which is of simplified construction and of improved usefulness and safety. The mechanical outlay is greatly reduced. No coordination between press button movement and inhalation is needed. The quantity is brought into the position ready for dispensing without any rush. The user can concentrate on inhaling the active substance. The inhaler is designed in concrete terms such that the metering device consists of a metering drum, the supply container for the drug being arranged in the interior of the metering drum, and that the air inlet channel and the connection channel run towards each other in a V-shape and towards a portioned-off quantity of drug present in the shape of a dome and provided by the metering drum at the apex of the two air channels. The interior of the metering drum is now used for forming a supply. Its content is kept in motion. It comes by the shortest route into the position ready for dispensing. Discharging with no residues remaining behind takes place there. As a result of the stated orientation and sequence of the operational areas, it is not possible for any particles to fall back. The suction stream impacts first on the V apex and flows into the exactly positioned and portioned-off, exposed heap of the drug. The zone presented in a dome-shape is quickly carried off, swirled and dispersed and, upon inhalation, reaches the target site. The drug is sucked counter to the effect of gravity. Incorrect holding is practically ruled out since the position of the metering drum suggests the correct handling, and it is readily apparent to the user that the mouthpiece channel situated at the other, upper, end is the transfer bridge. In addition, a potential for an overdose cannot build up; a non-inhaled inhalation quantity disappears in the direction of the supply. It is not added to by the next indexing step. An advantage in terms of flow technology proves to be the fact that the connection channel runs radially with respect to the metering drum. It is thus optimally suited to its function as acceleration channel with increasing abatement towards the top. In order to create a sufficiently large transfer area to the swirl chamber, which acts as a dwell-time chamber on the access side, the inhaler is advantageously designed such that the connection channel widens towards the swirl chamber, and the trace line of the one wall lies essentially radially with respect to the center of the swirl chamber, and that of the other wall runs essentially tangentially thereto. This leads to a flow which promotes swirling and which defines the direction of rotation. As regards the outlet mouthpiece channel, the construction in this case is chosen such that the mouthpiece channel runs at an obtuse angle with respect to the connection channel, and the trace line of the one wall is aligned approximately tangentially, and that of the other wall approximately radially, with respect to the center of the swirl chamber. A continuous cross-sectional widening (also in the transverse width) is also expediently made use of in this respect (realization of the diffusor effect sought). As regards the design of the air inlet channel, the procedure in this case is that the trace line of the inner wall and the trace line of the outer wall of the air inlet channel are aligned in secant formation with respect to the metering chamber. Suction opening and air outlet opening of the device are thus at a sufficient spatial distance from each other. As regards the design of the metering drum, this is continued such that it has a rotary sleeve equipped with portion apertures. The portion apertures arranged in a uniform angular distribution dip into the powder supply on account of the mixing-drum-like rotation of the metering drum, without causing pressing etc. The metering is correct in terms of volume, including the penultimate portion and, if appropriate, the final portion. Also, on account of the use of the drum movement, there is no agglomeration of the drug. It is further proposed that the rotary sleeve is formed by the circumferential wall of a pot, the base of which forms a rotary purchase. The correspondingly outwardly accessible rotary grip is extremely easy to use and direct. In order to obtain a defined position of the dome, that is to say of the metered quantity of the portioned-off drug, a catch mechanism determining the direction of rotation is allocated to the device between rotary sleeve and housing. As regards the rotary bearing of the metering drum and the obtainment of constantly uniform inhalation quantities of drug, it proves advantageous that the rotary sleeve enclosed by an outer wall is underpinned, over a partial angle area, by an inner wall section which, in the area of the V apex, forms the base of the portion chamber formed by in each case one of the apertures. In this context it is additionally advantageous that the transverse walls of the apertures run in a wedge formation to the center of the metering drum. This leads, as regards the transverse walls, to a convexly curved, trapezoidal trough as portion chamber which widens at the V apex side, in other words towards the top. A further development of the invention lies in the fact that, issuing from the base of the pot and/or the housing, loosening fingers protrude into the metering drum. They form a type of stirrer which, operating actively or statically, optimizes the loosening of the powdery drug (formulation). In order to eliminate the moisture which cannot be completely prevented, the base of the pot or the inner side of a housing-filling lid is allocated a drying agent chamber, which would be equipped as appropriate. Such a filling lid can be formed at the same time as a viewing glass. A good suction effect is achieved by arranging transversely directed air inlet slots at the intake end of the air inlet channel. The suction opening is thus prevented from being blocked, for example by loosely carried coins, etc. The grid-like design of the air inlet is also useful to the extent that no foreign particles, such as dust etc., can be sucked in. Such air inlet slots are expediently provided on both broad sides of the device housing. They lie in such a way that, when the inhaler is being handled, they cannot easily be closed over; in any case one or the other side remains open. The device is further characterized by a dividing gusset for the path of the air sucked in. Thus, a Y-channel is formed in practice on the suction side. In the event of incorrect use (blowing instead of sucking), in order to prevent the discharge of the powdery drug, the air inlet slots are allocated exhalation barrier tongues. Thus, on puffing, no respiratory air moisture reaches into the inside of the inhaler device, which is to be kept as completely dry as possible. These can be simple valve flaps. The abovementioned dividing gusset can be used for fitting them, as is explained in the relevant part of the description. For correct handling it is thus expedient for the air inlet slots to reach approximately to the height of the center of the swirl chamber. They are in this way sufficiently raised from the base area and cannot in practice be closed off by the hand of the user. One embodiment which is similarly useful for the purpose of correct handling is achieved by means of a finger depression lying approximately underneath the swirl chamber on the device housing. The finger depression at the same time provides a rest for the lower lip of the user, without the mouthpiece needing to have a projection exceeding the overall cross-section of the housing. A beak structure is obtained which is advantageous to use. The whole thing can in this case be covered by a protective cap engaging over the housing. The protective cap can be held on the housing in a simple manner by means of clamping, snap locking etc., so that the device can be released only by deliberately pulling on the protective cap. To this extent, account is also taken of the relevant hygienic requirements. In order also to eliminate moisture present in the mouthpiece area during periods when the device is not in use, the protective cap is also allocated a drying agent chamber. A further improvement which is favourable particularly in terms of production technology is that all air channels and the swirl chamber are incorporated in a support structure which can be enclosed by two housing shells and in which the metering drum is also mounted, the housing shells forming the covering for the air channels and the swirl cheer. In addition, provision can be made for the support structure to form the stand for the device when it is designed as a standing unit, the shoulder of the support structure forming a push-on limit stop for the protective cap. Finally, a feature of the channel structure which is of interest in terms of flow technology is that the wall section of the swirl chamber directed towards the upper end of the connection channel has a smaller curvature and consequently assumes a significantly flatter course, and a central passage of the swirl chamber is arranged eccentric to the said wall section. This "flattening" of the upper semicircle has the surprising effect that a tendency towards settling, which can generally be observed there, is essentially reduced or practically no longer occurs. Instead of a purely circular flow path, there is a relatively ascending flow path with a stronger flow effect, which reliably entrains the particles which have a tendency to adhere.

The following additional advantages are achieved with the invention:

The inhaler is also suitable for drug formulations with poor flow or which have a tendency to cake. As a result of the simultaneous homogenization upon each metering operation, any powder bridges present are broken up and loosened.

It has moreover been found that in the event of slight deviations from the prescribed use position the metering accuracy is not appreciably impaired; i.e. slight deviations from the use position are not critical in respect of the metering accuracy. After the metering, i.e. after actuation of the metering drum, the inhalation can take place in any desired position.

On account of the construction being amenable to injection-moulding and on account of the small number of necessary components, the inhaler can be produced cost-effectively and economically in large batch quantities.

The particular flow design downstream of the discharge from a portion chamber in the metering drum has the result that a high proportion of respirable powder particles is generated.

The subject matter of the invention is discussed in greater detail hereinbelow on the basis of an exemplary embodiment which is illustrated in the drawings, in which.

Figure 1:
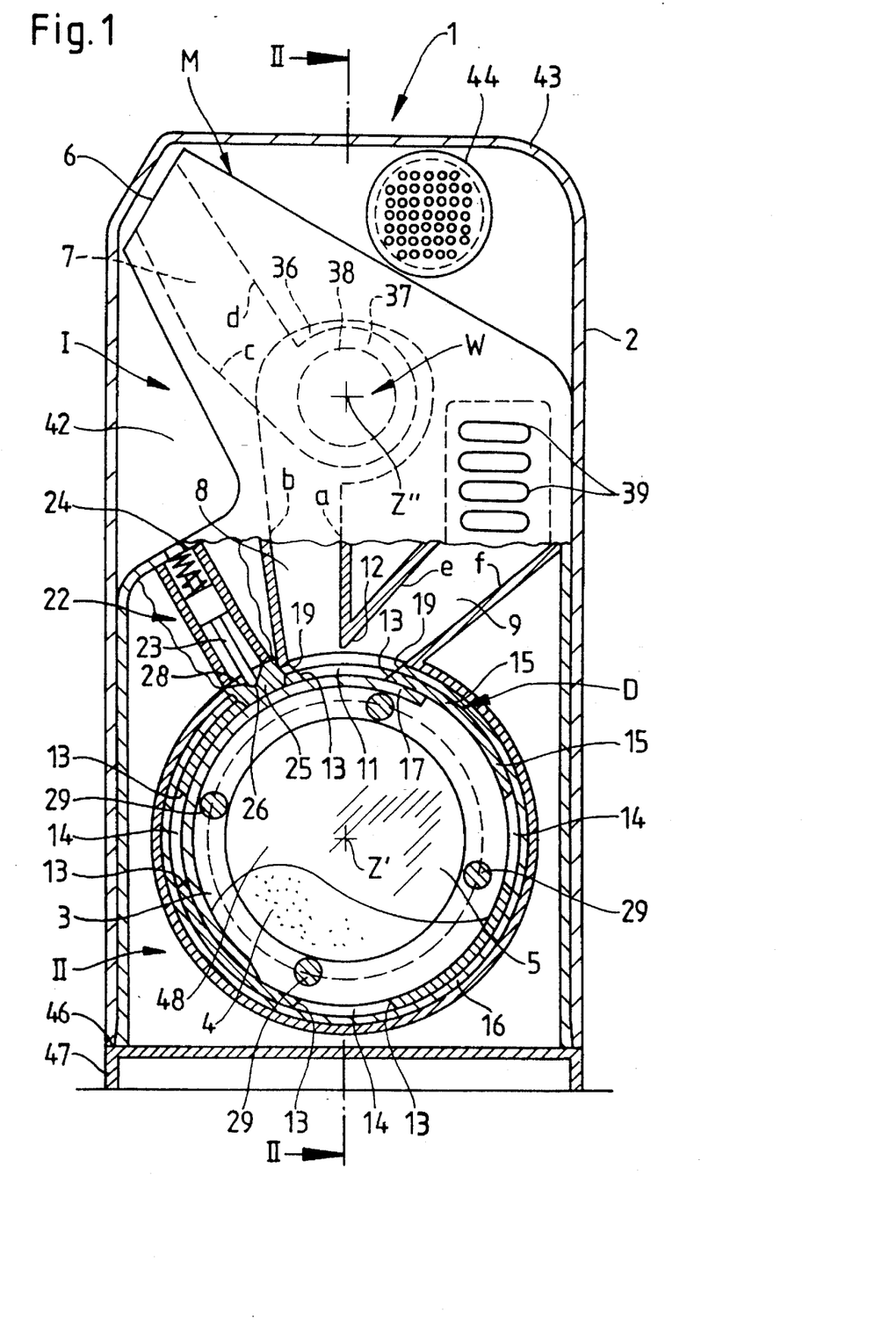
FIG. 1 shows the device for inhalation of a powdery drug, in partial vertical section along line I—I in FIG. 2, and with the protective cap in full section.
Figure 2:
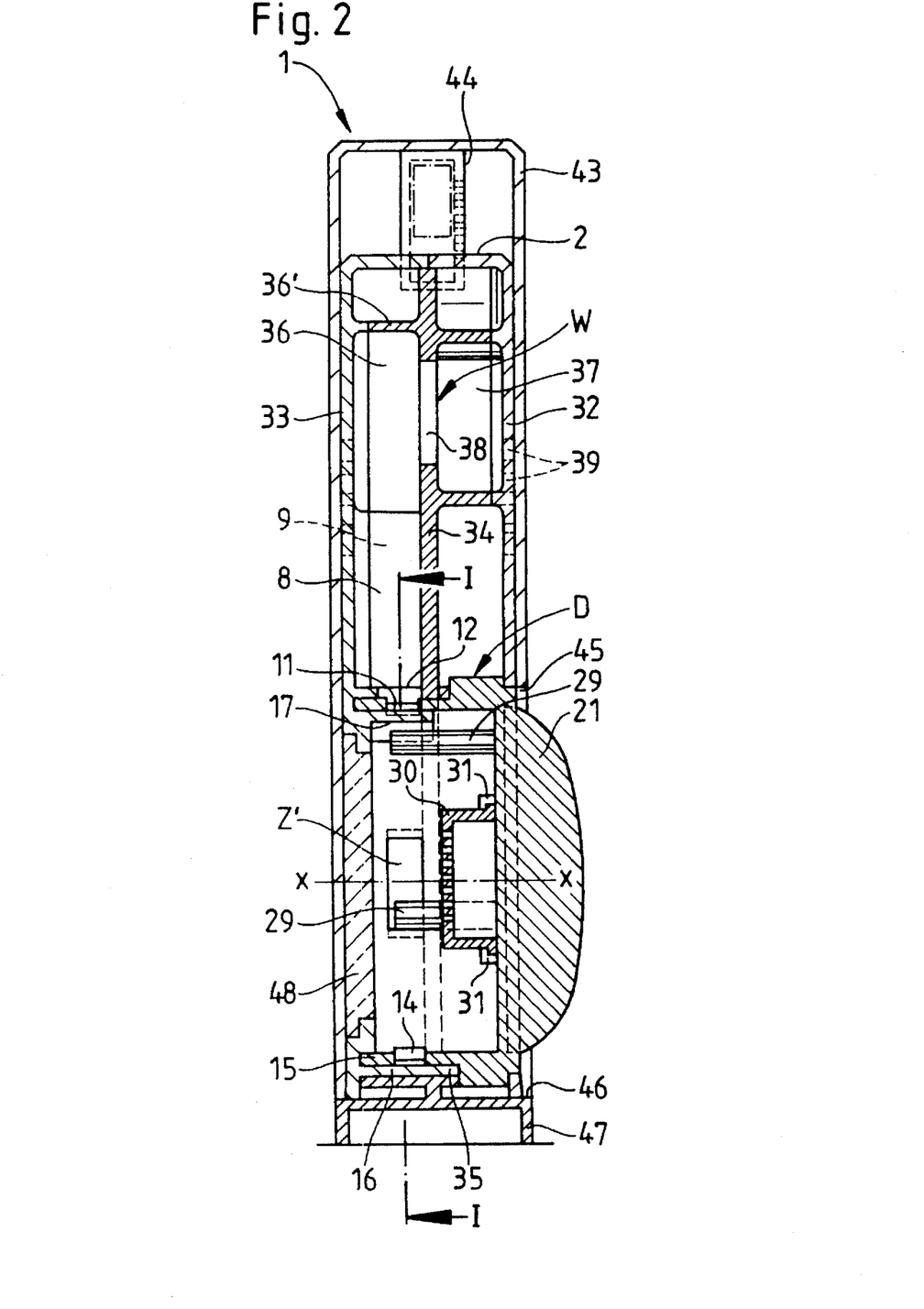
FIG. 2 shows the section along line II—II in FIG. 1.
Figure 3:
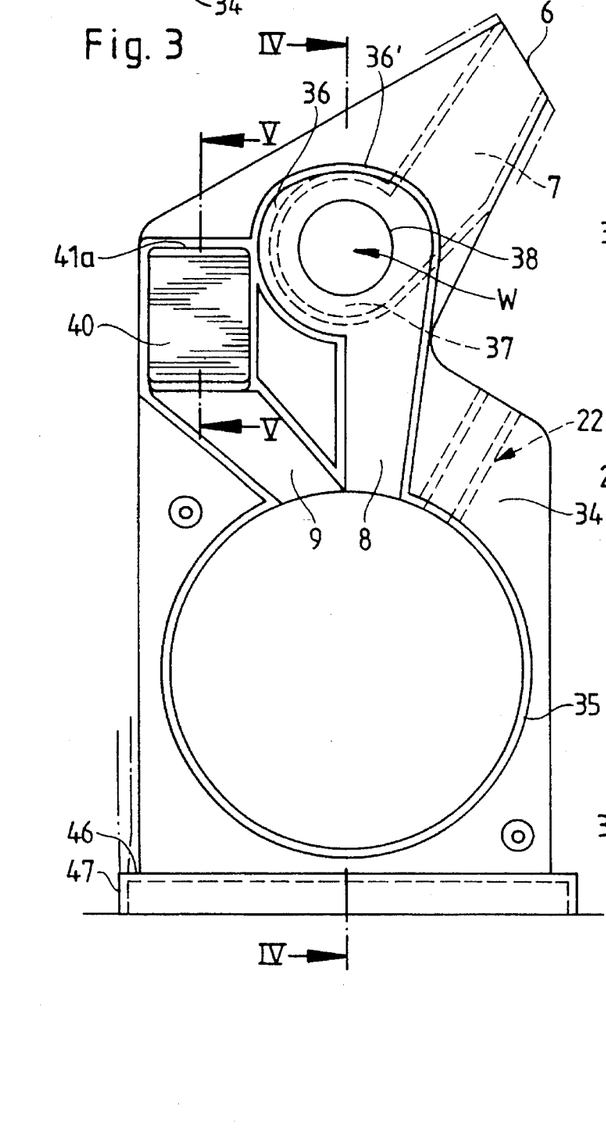
FIG. 3 shows a support structure, contributing to the channel structure etc, of the housing shown in isolated representation in a side view.
Figure 4:
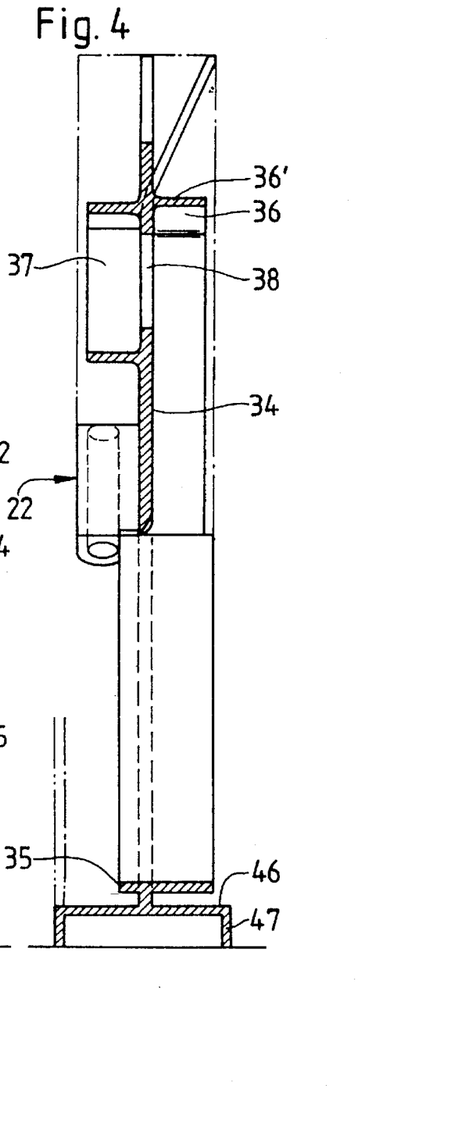
FIG. 4 shows the section along line IV—IV in FIG. 3.

The device designed as a pocket appliance, referred to hereinbelow as inhaler 1, has, in accordance with FIGS. 1 and 2, a long rectangular, flat housing 2 designed in pocket format. Its head area contains a so-called dispersing part I and its foot area contains a metering part II. In the description which follows it is assumed that the inhaler 1 is situated in a vertical plane which corresponds to the drawing plane in the figures, i.e. as represented in FIGS. 1 to 2, the dispersing part I is arranged above the metering part II.

The metering part II comprises a supply container 3 which is filled with a powdery drug 4 (formulation).

The supply container 3 is formed by the interior 5 of a metering drum D. The metering drum D is mounted rotatably in the housing 2 and can be actuated directly by hand from the outside. It is situated in the foot area of the inhaler 1 and in terms of volume utilizes almost the whole width of the housing 2. The geometric, horizontal axis of rotation of the metering drum D is designated x—x (FIG. 2).

Situated above the metering drum D, which serves for providing a portioned-off inhalation quantity of drug, there is a swirl chamber W.

The swirl chamber continues into an upwardly directed mouthpiece M which, at the highest point of its beak-shaped structure, forms an outlet opening 6 fitting the mouth.

When it is being used, the inhaler is held in such a way that the metering part II is situated at the bottom and the dispersing part I with the mouthpiece M is situated at the top (use position). This position also corresponds to the representation chosen in FIG. 1 and FIG. 2.

Thus, metering drum D, swirl cheer W and mouthpiece channel 7, which connects the swirl chamber W and the outlet opening 6 to each other and forms, with its surround, the mouthpiece M, in practice lie vertically one above the other in the use position of the inhaler 1. The powdery particles are therefore conveyed from the bottom upwards during inhalation.

Issuing from the swirl chamber W is a downwardly directed connection channel 8. The latter is joined, in the area of the provision of a predetermined (portioned-off) inhalation quantity of drug, to an air inlet channel 8 leading to the outside.

Figure 19:
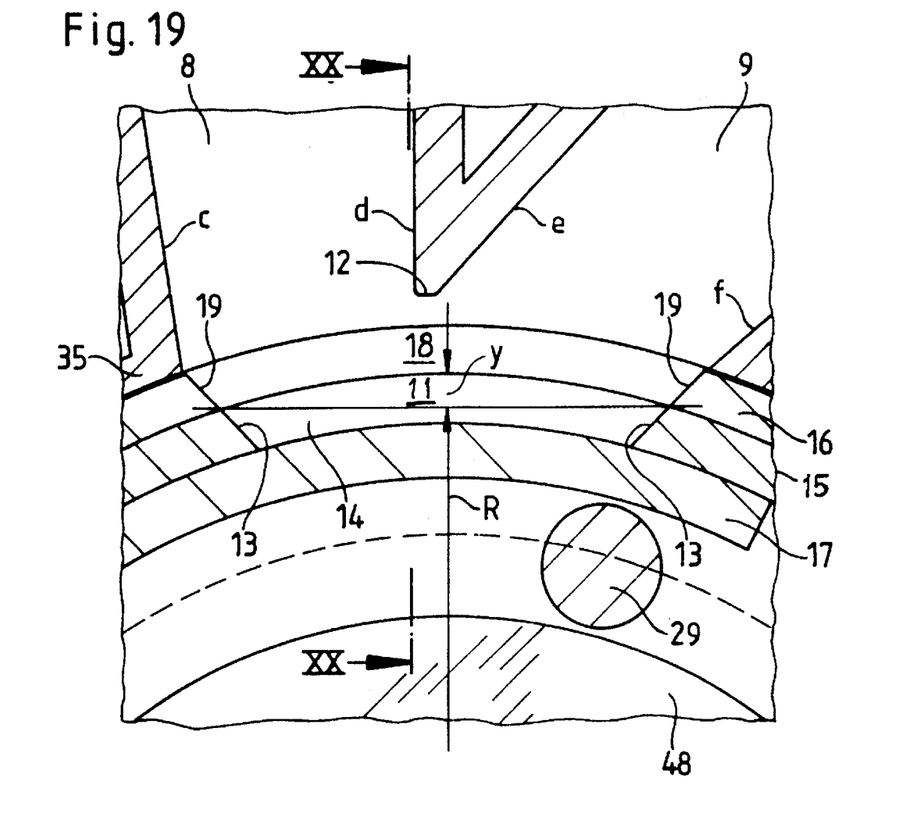
FIG. 19 shows an enlargement of the V apex area forming the portion chamber.
Figure 20:
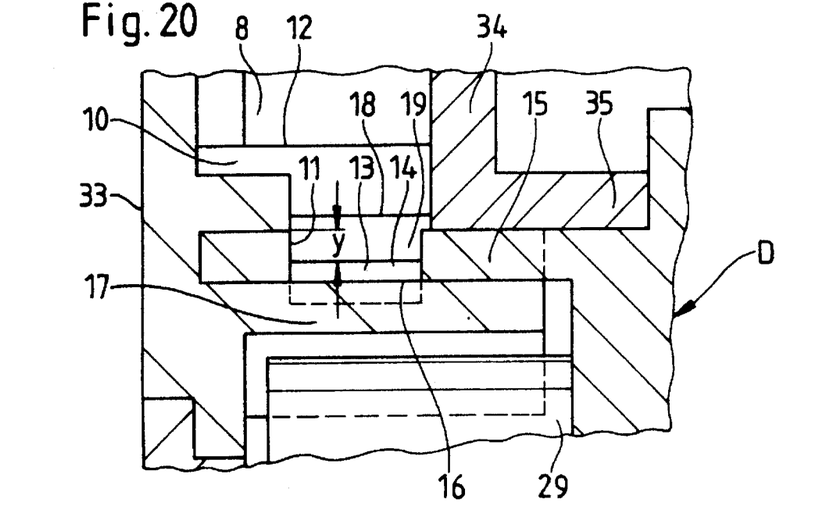
FIG. 20 shows the section along line XX—XX in FIG. 19.

Air inlet channel 9 and connection channel 8 run in a V-shape towards each other and towards the periphery of the metering drum D. This forms an acute-angled channel structure (about 50°), at the V-shaped apex area of which the exactly metered quantity of powder removed from the supply container 3 is exposed to the suction air stream so as to be discharged. For this purpose, the metering drum D has portion cheers 11 open towards the channel side. As a result of the circular curvature of the metering drum D, the portioned-off drug (formulation) is prepared as a layer bulging in the direction counter to the cause of the bend. The resulting dome shape of the drug can be cleared off and out in a manner particularly favourable in flow terms. The convex curvature pointing in the direction of a channel-dividing point 12 of the channels 8 and 9 is particularly clear from FIG. 19. There, the additional height y (indicated in the chord center), resulting from the curvature of the chamber 11, of the radial R directed towards the center Z' of the metering drum D can be clearly seen. The center Z' lies on the abovementioned geometric axis of rotation x—x.

As is clear from FIGS. 1, 2, 12 to 14, 16, and in particular 19, a portion chamber 11 is formed by an aperture 14 in a rotary sleeve 15 of the metering drum D designed as a pot. According to FIG. 1, four apertures 14 are distributed uniformly about the circumference of the rotary sleeve 15. The apertures 14 are delimited by side walls 13 which are bevelled in such a way that the apertures 14 taper towards the center Z' of the metering drum D. The bevel angle lies at 45° to the shortest connection between inner and outer surface of the metering drum wall. The transverse walls 13 give the portion chamber 11 the shape of a trapezoidal, outwardly opening, curved trough of considerably greater length than width.

The rotary sleeve 15 is mounted rotatably between an annular wall 16 and a likewise annular wall section 17 extending through a curve angle of approximately 180°. The approximately semicircular, web-shaped wall section 17 is in this case arranged in such a way that, on the one hand, at the zenith of the metering drum D it extends beyond the V-shaped apex area of the air channels 8 and 9 to such a degree that at no point is there a through-connection between the air channels 8 and 9 and the supply container 3, and, on the other hand, at the lower end it leaves the foot area of the rotary sleeve 15 free (see FIG. 1). The annular wall 16 and the wall section 17 are integrally formed on the housing 2. The bearing of the rotary sleeve can be improved by means of an approximately 1 to 2 mm high bearing collar which extends in a continuation of the said wall section 17 through the remaining circumference angle and is likewise integrally formed on the housing 2. In this way the circumferential surface of the rotary sleeve 15 can be guided with precision in the annular gap between the annular wall 16 and the wall section 17, including the said bearing collar. The annular wall 16 has an inlet window 18 opposite the channel-dividing point 12 of the air channels 8 and 9. The side surfaces 19 of the inlet window 18 are bevelled such that they are flush with the side surfaces 13 of the portion chamber 11 when this portion chamber 11 is situated exactly under the inlet window 18. As long as a portion chamber 11 is situated within the angle range of the wall section 17, the outer surface of the wall section 17 functions as a base 16 for the trough-shaped portion chamber 11. For this reason, the height of the web-shaped wall section 17 is dimensioned slightly greater than the width of the aperture 14. Upon a further rotation of the metering sleeve 15 in the clockwise direction, i.e. after the portion chamber 11 under the inlet window 18 has advanced beyond the right upper end of the wall section 17, the base of the portion chamber 11 is open, so that it is once again in communication with the interior 5 and with the supply container 3.

The channel-dividing point 12 directed approximately towards the transverse center of the portion chamber 11 lies at a distance from the wall section 17 lying underneath, which distance amounts to approximately half the transverse dimension of the V-apex end of the connection channel 8 and air inlet channel 9. This leads to a high flow velocity in the area of the bend, with the result that the portion chamber 11 filled with the powdery drug is emptied without leaving residues behind upon inhalation, even in a critical position of the inhaler.

Whereas the said wall section 17 in the area of the V apex functions with its outer surface as a base 16, in the area of the rising portion chamber, upstream in the clockwise direction, it shields from the inside the inhalation quantity, taken from the powder supply, of the next aperture 14 from the supply container. In FIG. 1 this portion chamber is situated in a "9 o'clock" position, while the portion chamber ready for inhalation is in a "12 o'clock" position. The charging of a portion chamber 11 is effected by means of the associated aperture 14 being pushed forwards under the powder supply 4 upon further rotation of the metering sleeve 15 (in FIG. 1 approximately in a zone from "4 o'clock" to "7 o'clock"), this portion chamber 11 thus filling with the powder. Upon further rotation of the metering sleeve 15, this portion chamber comes into the ascending area between "6 o'clock" and "9 o'clock". In this area the quantity of the inhalation dose in the portion chamber is protected by the shielding effect of the wall section 17, the lower end of which functions as a stripper, so that any inwardly directed surplus powder is scraped off. In this way an exact inhalation dose with reproducible powder density is achieved.

The wall section 17 leaves a good 180° open to the interior 5 of the supply container 3. The rotary sleeve 15 acts as a rotary slide. If the metered inhalation quantity is not removed, then upon further rotation of the metering drum D it returns automatically to the supply, in other words to the supply container 3. Quantity accumulation is not possible. This important advantage results from the vertical orientation of the functional members.

Figure 16:
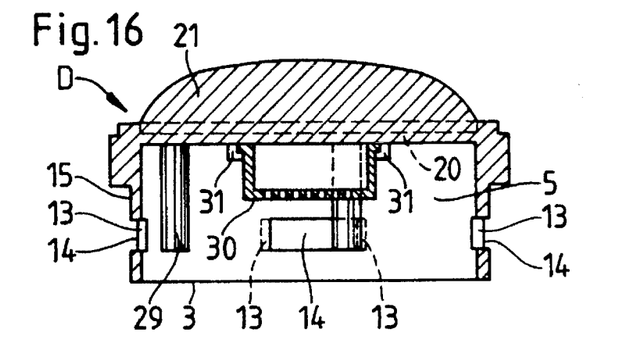
FIG. 16 shows the section along line XVI—XVI in FIG. 15.
Figure 17:
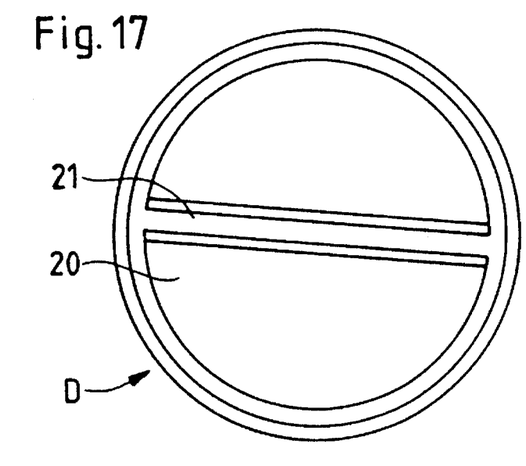
FIG. 17 shows the metering drum in isolated representation, as viewed towards its rotary grip.

The circumferential wall of the rotary sleeve 15 of the pot-shaped metering drum D merges outwardly into a pot base 20 which closes the supply container 3 and on the outside of which an easily accessible turning knob 21 is arranged (see in particular FIG. 16 and FIG. 17).

The metering drum D has a catch mechanism 22 which is designed for rotation in the clockwise direction. The main component of this mechanism is a radially movable locking pin 23 which is loaded by a compression spring 24 in the engagement direction. The opposite catch means consist of opposite catches 25 which lie on the circumference of the rotary sleeve 15 and of the metering drum D and which are positioned in such a way that the ready-to-dispense position of the portion chamber 11 is obtained exactly step by step. The opposite catch 25 is equipped with edges which are such that, when the catch is intentionally overcome, the metering drum D locked in the respective ready-to-dispense position can be rotated further, while a rotation in the opposite direction is not readily possible on account of a steeper edge. A reversal of the direction of rotation is of course possible if the device is to be designed specially for left-handed users.

Figure 18:
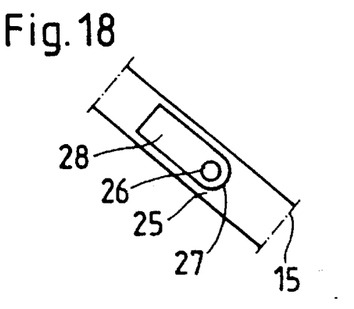
FIG. 18 shows the detail of the catch mechanism facing the metering-drum side.

The actual catch depression of the opposite catch 25 is designated in FIG. 18 by 26, the steeper edge by 27, and the less inclined edge, which can be overcome if so intended, by 28. The opposite catch 27 lies in a flange section of the rotary sleeve 15 having a thickened wall and lying nearer the pot base 20 of the metering drum D.

Arranged on the pot base 20, parallel to the axis of rotation of the metering drum D and distributed uniformly about the circumference, are a plurality of loosening fingers 29 which project into the powder supply and whose radial distance from the center is chosen such that, upon rotation, they scrape along the back of the wall section 17, so that no powder can settle there. According to FIG. 1, one loosening finger 29 is arranged, as seen in the clockwise direction, directly behind each aperture 14 (leading). Alternatively, or in addition to this, the loosening fingers can be arranged stationary on the housing 2, in which case the drum movement is similarly used for loosening the powder.

Situated in the center of the base 20, likewise on the inner side thereof, that is to say projecting into the supply container 3, is a drying agent chamber 30. This is, for example, a capsule which can be secured by means of a clip fastening and whose base is permeable to water vapour. Clip lugs 31 engaging over the edges serve to hold the capsule in position.

The inhaler housing 2 consists of two housing shells 32 and 33 of U-shaped cross-section. The two shells 32 and 33 enclose, in sandwich fashion, a support structure 34 as core part, in which there are accommodated, as main components, the connection channel 8, the air inlet channel 9 with flow separation at the inlet side, the swirl chamber W, the mouthpiece channel 7, a circular recess 35 for the mounting of the metering drum D, and the catch mechanism 22. The air channels 7, 8, 9 are incorporated into the support structure 34 in the form of groove-like depressions of approximately rectangular cross-section, and the air chambers are incorporated into the support structure 34 in the form of essentially circular recesses, and they are closed off and covered by the housing shells 32 and 33. This construction guarantees a sufficient mechanical stability, even when the support structure 34 is designed with relatively thin walls (e.g. about 5 mm) for reasons of reducing weight.

Figures 9, 10:
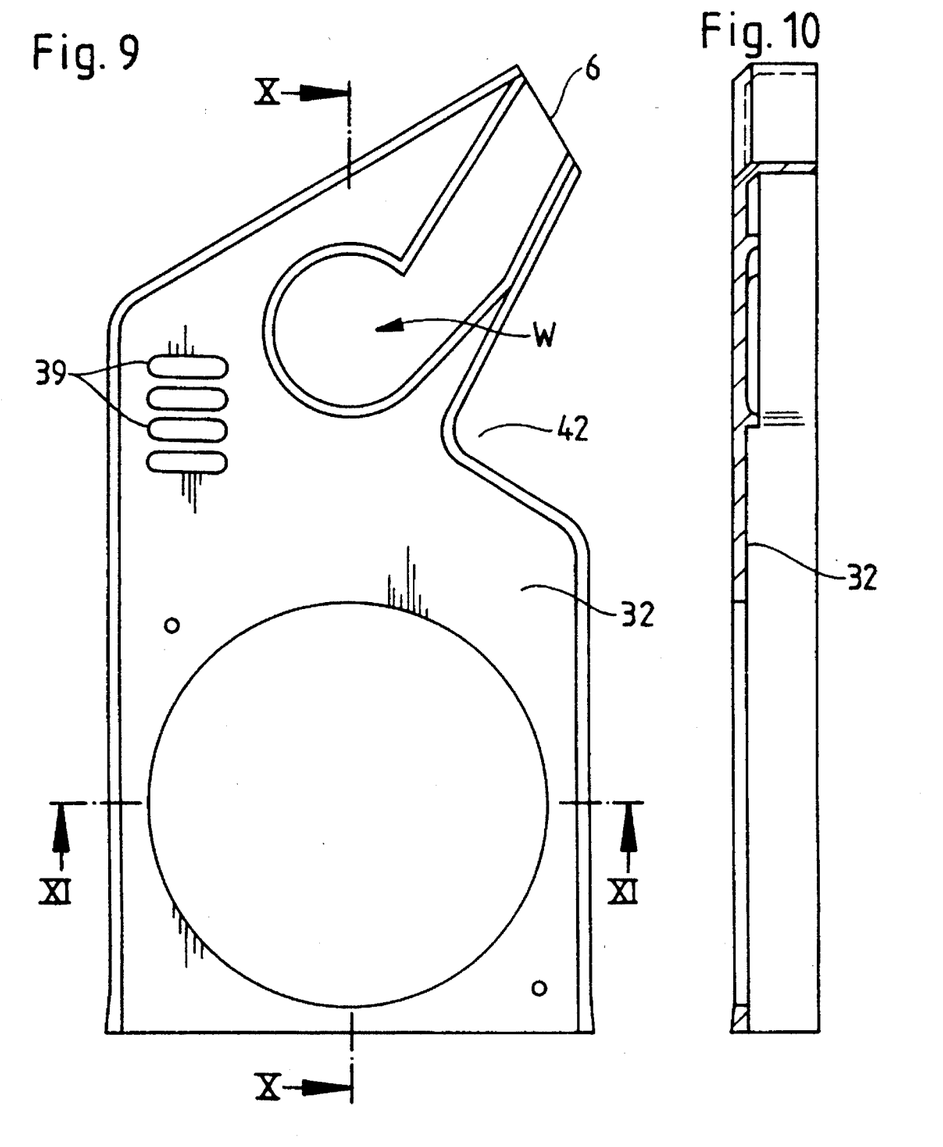
FIG. 9 shows an inside view towards the right-hand shell of the housing.
FIG. 10 shows the section along line X—X in FIG. 9.
Figure 11:
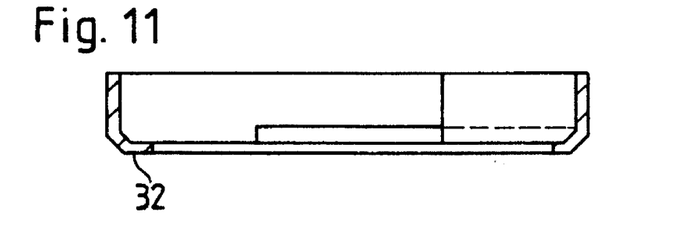
FIG. 11 shows the section along line XI—XI in FIG. 9.
Figure 12:
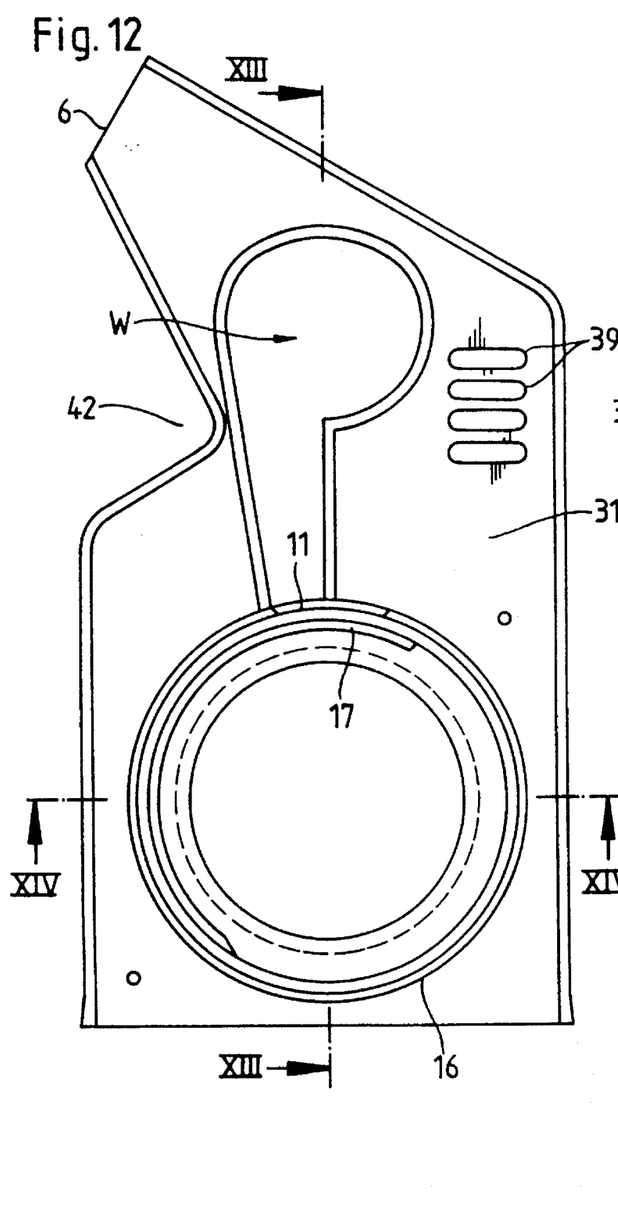
FIG. 12 shows an inside view towards the left-hand shell of the housing.
Figure 13:
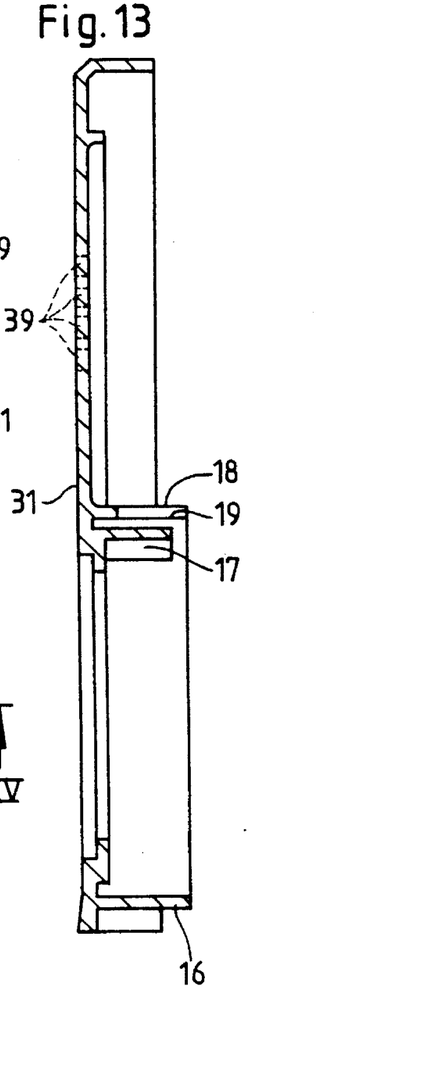
FIG. 13 shows the section along line XIII—XIII in FIG. 12.
Figure 14:
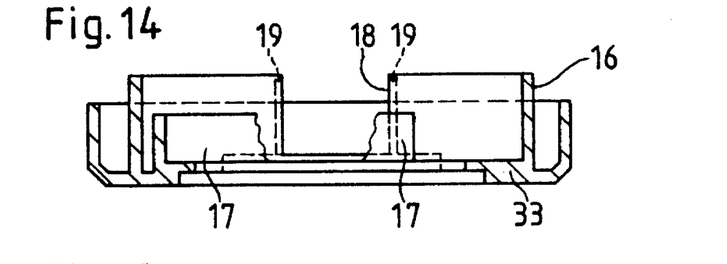
FIG. 14 shows the section along line XIV—XIV in FIG. 12.
Figure 15:
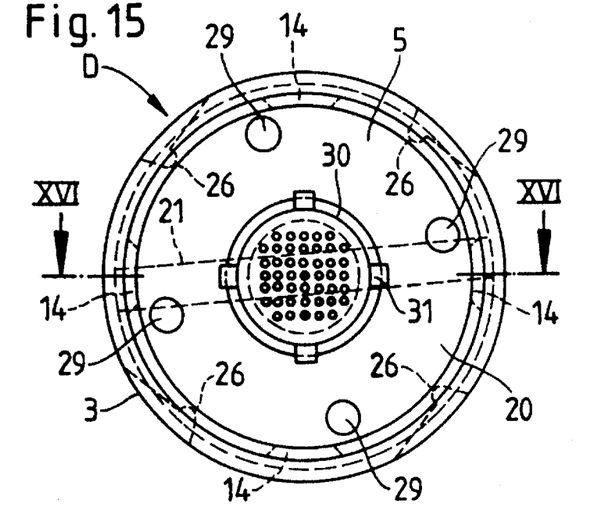
FIG. 15 shows the metering drum in isolated representation, as viewed into the pot cavity.

The support structure 34 is represented in FIGS. 3 to 7, the right-hand housing shell 32, as viewed according to FIG. 2, is shown in FIGS. 9 to 11 in isolated representation, and the left-hand housing shell 33 is shown in FIGS. 12 to 14. Ridges moulded integrally on the inner sides of the shell abut against each other via their end faces and against oppositely directed ridges of the support structure 34 which is held between them. The manner of fastening the parts can be based on a clamping technique; an adhesive bonding or thermal bonding is also conceivable, unless it is desired that the housing 2 should be able to be taken apart completely or partially for cleaning purposes and refilling purposes. In this case the usual traditional fastening means are to be preferred, such as screwing etc.

The connection channel 8 is aligned in the support structure 34 in such a way that it runs essentially radially to the metering drum D. While it tapers slightly in this direction, it widens continuously in the opposite direction. The extent to which the connection channel 8 widens towards the swirl chamber is shown clearly in FIG. 1 and FIG. 3. It can also be seen from these that the trace line of the one channel wall a runs radically with respect to the center Z" of the circular swirl chamber W and that the trace line of the other wall b runs tangentially with respect to the swirl chamber. The connection channel 8 and swirl chamber W thus present an outline which can be likened to a whistle. The swirl chamber is designed in two parts, and the two chamber parts, the dwell-time chamber 36 and the outlet chamber 37, lie alongside each other, viewed perpendicular to the housing shells 32 and 33, and communicate with each other via a central, transversely directed, circular passage 38. A saliva guard is formed by means of this arrangement. It has been found that a settlement or adhesion of the powder in the dwelltime chamber 36 and the outlet chamber 37 can be substantially avoided if the volume of the chambers is reduced by inwardly directed impressions in the housing shells 32 and 33. The circular outlet chamber 37, while forming the above mentioned whistle profile, continues upwards into the mouthpiece channel 7. The mouthpiece channel 7 running at an obtuse angle to the connection channel 8 is designed in such a way that the trace line of one wall c is directed tangentially, and that of the other wall d approximately radially, with respect to the center Z" of the swirl chamber W. Halfway along its length the wall c has a bend for the purpose of forming a slight narrowing towards the outside.

The air inlet channel 9 is aligned in such a way that the trace line of the inner wall e, leading to the channel-dividing point 12, and that of the outer wall f of the air inlet channel 9 are aligned in a secant formation with respect to the metering drum D.

The inhalation air is sucked in from the outside and through the air inlet channel 9 via air inlet slots 39. Half of the air inlet slots are arranged on the housing shell 32 and the other half on the opposite housing shell 33, so that the suction air stream is divided into two partial streams before entry into the air inlet channel 9. For this purpose, a splitting of the air inlet channel 9 is provided for in the support structure 34. The splitting is obtained by means of a dividing gusset 40 which combines the partial streams sucked in from both broad sides of the device into one suction stream (see FIG. 1 and FIGS. 3 to 6). Whereas the outlet chamber of the swirl chamber W is circular, the dwell-time chamber 36 has a shape deviating from a circular cross-section. As can be seen from FIG. 3, the wall section 36' facing towards the upper end of the connection channel 8 has a slighter curvature and, consequently, a significantly flatter course than does the greater part of the dwelltime chamber 36. The central passage of the swirl chamber W is arranged eccentrically relative to this flattened part 36".

This "flattening" leads surprisingly to a better removal of powdery drug which may possibly have settled.

The distinct flattening extends over only the upper semicircle of the swirl chamber W; the lower half, which is interrupted by the upper end of the connection channel 8, is circular, that is to say concentric with respect to the center Z" of the swirl chamber W.

Figure 5:
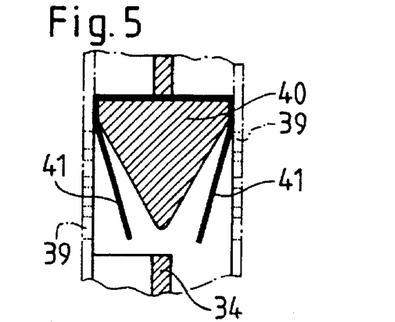
FIG. 5 shows the section along line V—V in FIG. 3, representing the dividing gusset, which divides the suction path, as well as the exhalation barrier.

In order to prevent the discharge of the inhalation quantity of drug in the event of incorrect operation of the inhaler 1, that is to say when blowing instead of sucking, two exhalation barrier tongues 41 are arranged in the flow path of the dividing gusset 40 in the area of the air inlet (see FIG. 5). They act as nonreturn valves, with the inside edge of the air inlet slots 39 forming the corresponding valve seat surface. Such an exhalation barrier tongue 41 is of simple construction and consists of a rubber or plastic strip section of appropriate flexibility. The latter is simply placed over the dividing gusset 40 of triangular cross-section and is clamped to the wall of the support 2 in a retaining slot 41a. The point of the dividing gusset 40 is directed downwards.

The function of the exhalation barrier tongues 41 is also assured from the point of view of ergonometrics, since the inlet slots 39 reach only to about the height of the center Z" of the swirl chamber W. The air inlet slots 39 thus lie in the head area of the inhaler 1, while the foot area thereof is free for gripping. FIG. 1 in particular also shows a beak-like configuration of the said head of the inhaler 1. The mouthpiece M tapers continuously to the free end, while at the other end a finger depression 42 is provided beside and essentially underneath the swirl chamber W. Not only is the use of the inhaler 1 facilitated in this way, but the correct handling thereof is also suggested. When the inhaler is being used, the lower lip of the user rests on the side surface of the mouthpiece above the finger depression 42.

The said finger depression 42 is designed such that the thumb can be placed comfortably thereon.

Figures 6, 8:
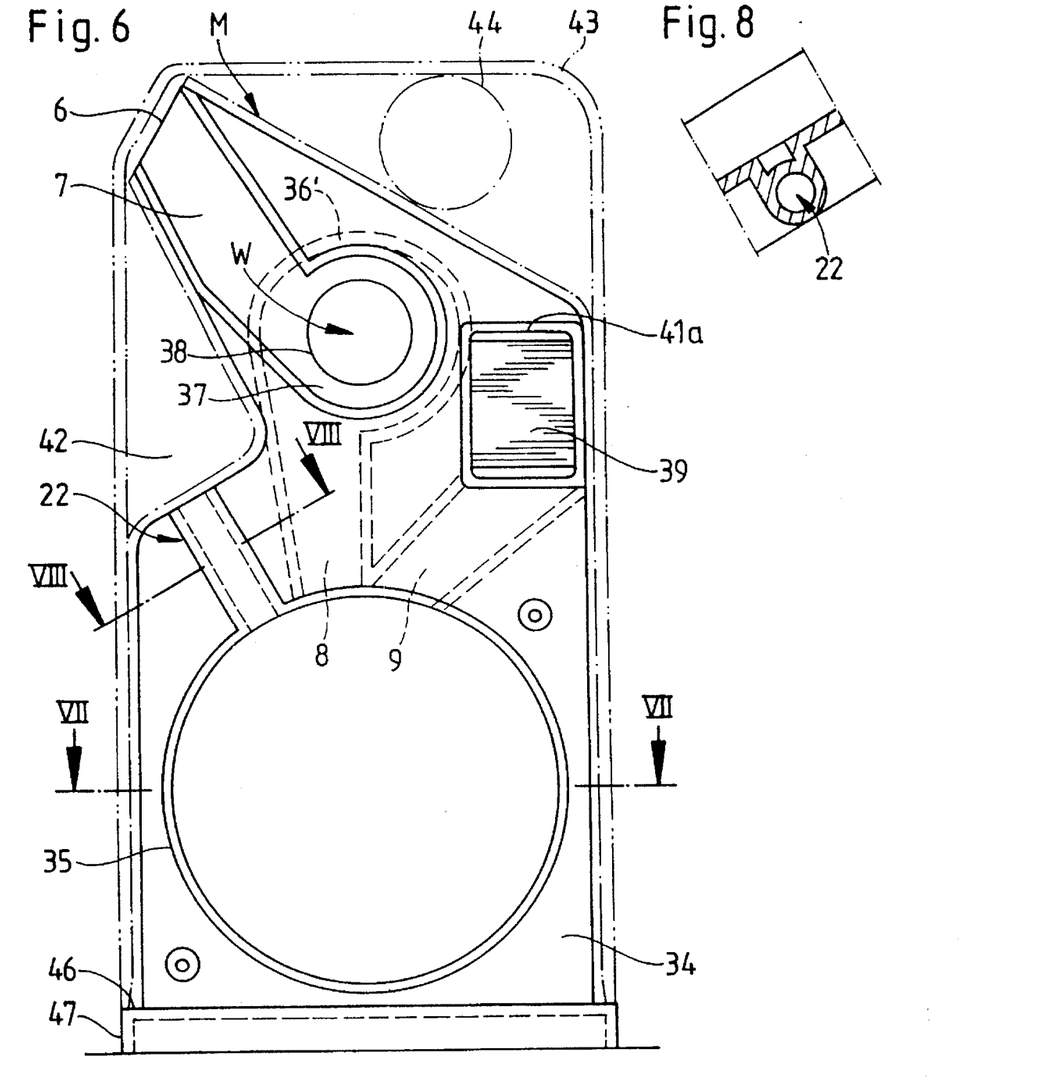
FIG. 6 shows the support structure in isolated representation, viewed from the other broad side.
FIG. 8 shows the section along line VIII—VIII in FIG. 6, representing the seat for the catch mechanism.
Figure 7:
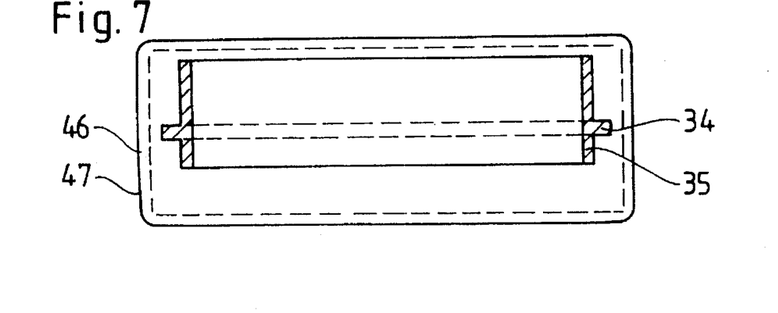
FIG. 7 shows the section along line VII—VII in FIG. 6.

A protective cap 43 engaging over the inhaler 1 is used in the interest of hygiene (see FIG. 6). It likewise has, in the lid area, a drying agent chamber 44 which is accommodated in the space remaining free between protective cap 43 and mouthpiece M. The protective cap 43 is recessed in the area of the turning knob 21 (recess 45).

An upper, level shoulder 46 of a stand 47 formed integrally on the support structure 34 serves as a limit stop for the protective cap 43. The shell walls are slightly flared in this area, so that the lower edge of the protective cap 43 is held secure by means of a clamping fit.

The protective cap 43 engages over the broad sides and narrow sides of the housing 2 which are formed by the shells 32 and 33, and also over the upper end face of said housing.

On the broad side lying opposite the turning knob 21, the supply container 3 has a transparent, disc-shaped section 48 as viewing window (see FIG. 2). In this way the powder content can be checked. The said viewing window at the same time acts as a filling lid. The latter could also serve as for the support static loosening fingers 29, if this version were to be constructed. The drying agent chamber 30 described could also be situated on the inner side of the filling lid.

The functioning of the inhaler 1 is, in brief, as follows: The air sucked in through the air inlet channel 9 flows, upon inhalation, into the portion chamber 11 filled with the metered quantity and carries the drug 4 into the upwardly directed flow path, i.e. into the connection channel 8. The the flow velocity decreases as it passes into the area of the swirl chamber W lying above. Here the air current passes into the dwell-time chamber 36, with decreasing velocity and counter to the force of gravity of the particles, and from there crosses transversely through the central passage 38, with further deceleration, into the outlet chamber 37. The powder/air mixture finally reaches the foot area of the mouthpiece channel 7, which acts as dispersing chamber. From the adjoining diffusor, which is formed by the upper end of the mouthpiece channel 7, the medicament passes via the outlet opening 6 to the target site (bronchi, lung). The flow path in the dispersing part I resembles two successive loops of the same direction of rotation.

By virtue of the continuous decrease in the flow velocity as far as the outlet opening 6 on the mouthpiece channel 7, the likelihood of impact separation of relatively small particles in the throat area is greatly reduced.

We claim:

1. Device for inhalation of a powdery, pharmacologically active drug, consisting of a housing (2), a supply container (3) for the drug (4), a manually actuated metering unit for providing a portioned-off quantity of inhalation substance which is picked up by the air current drawn in during inhalation and is swirled, an air inlet channel (9), having an inner wall (e) and an outer wall (f) a swirl chamber (W), having a center (Z") and a connection channel (8), having one wall (a) and another wall (b), between the swirl chamber (W) and the metering unit, as well as a mouthpiece channel (7), having one wall (c) and another wall (d), issuing from the swirl chamber (W), characterized in that the metering unit consists of a metering drum, the supply container (3) for the drug being arranged in the interior (5) of the metering drum D, having a center Z', and that the air inlet channel (9) and the connection channel (8) run towards each other in a v-shape and towards a portioned-off quantity of drug present in the shape of a dome and provided by the metering drum at the apex of the two air channels (8) and (9).

2. Device according to claim 1, characterized in that the connection channel (8) runs radially with respect to the metering drum (D).

3. Device according to claim 1, characterized in that the connection channel (8) widens towards the swirl chamber (W), and that one wall (a) of swirl chamber (W) lies essentially radially with respect to the center (Z") of the swirl chamber (W) and that the other wall (b) of swirl chamber (W) runs essentially tangentially thereto.

4. Device according to claim 1, characterized in that the mouthpiece channel (7) runs at an obtuse angle with respect to the connection channel (8), and that one wall (c) is directed approximately tangentially, and the other wall (d) approximately radially, with respect to the center (Z") of the swirl chamber (W).

5. Device according to claim 1, characterized in that the inner wall (e) and outer wall (f) of the air inlet channel (9) are directed in secant formation with respect to the metering drum (D).

6. Device according to claim 1, characterized in that the metering drum (D) has a rotary sleeve (15) equipped with portion apertures (14).

7. Device according to claim 6, characterized in that the rotary sleeve (15) is formed by the circumferential wall of a pot, on a base (20) of which a turning knob (21) is arranged.

8. Device according to claim 7, characterized by a catch mechanism (22), determining the direction of rotation, between rotary sleeve (15), having apertures (14) with side walls 13, and housing (2) of the device.

9. Device according to claim 8, characterized in that the rotary sleeve (15) is surrounded by an annular wall 16 and is underpinned, over a partial angle range, by an inner wall section (17) which, in the area of the V apex, forms the base of a portion chamber (11) formed by in each case one of the apertures (14).

10. Device according to claim 9, characterized in that the side walls (13) of the apertures (14) run in a wedge formation in the direction of the center (Z') of the metering drum (D).

11. Device according to claim 10, characterized in that, issuing from the base (20) of the pot and/or from the housing (2), loosening fingers (29) protrude into the metering drum (D).

12. Device according to claim 11, characterized in that a drying agent chamber (30) is allocated to the base (20) of the pot.

13. Device according to claim 12, further comprising transversely directed air inlet slots (39) arranged at the intake end of the air inlet channel (9).

14. Device according to claim 1, characterized in that a finger depression (42) is arranged on the inhaler housing (2) below the swirl chamber (W).

15. Device according to claim 1, characterized by a protective cap (43) engaging over the housing (2).

* * * * *